(12) United States Patent
Clerc et al.

(10) Patent No.: US 7,993,387 B2
(45) Date of Patent: Aug. 9, 2011

(54) STENT WITH REDUCED WELD PROFILES AND A CLOSED-END WIRE CONFIGURATION

(75) Inventors: Claude O. Clerc, Marlborough, MA (US); Paul K. Norton, Lunenburg, MA (US); Michael Zupkofska, Rockland, MA (US); Gary J. Leanna, Holden, MA (US); George Tom Roberts, Lincoln, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 652 days.

(21) Appl. No.: 10/845,844

(22) Filed: May 14, 2004

(65) Prior Publication Data

US 2005/0256563 A1 Nov. 17, 2005

(51) Int. Cl.
*A61F 2/86* (2006.01)
(52) U.S. Cl. .................. 623/1.15; 623/1.53; 623/1.13
(58) Field of Classification Search .............. 623/1.15, 623/1.16, 1.18, 1.31, 1.32, 1.33, 1.22, 1.49, 623/1.5, 1.51, 1.53, 1.54
See application file for complete search history.

(56) References Cited

U.S. PATENT DOCUMENTS

| | | | |
|---|---|---|---|
| 5,836,964 A * | 11/1998 | Richter et al. ............. 606/194 |
| 6,083,257 A | 7/2000 | Taylor et al. | |
| 6,187,036 B1 * | 2/2001 | Shaolian et al. ............ 623/1.15 |
| 6,241,757 B1 * | 6/2001 | An et al. ..................... 623/1.1 |
| 6,264,689 B1 | 7/2001 | Colgan et al. | |
| 6,325,825 B1 | 12/2001 | Kula et al. | |
| 6,387,123 B1 * | 5/2002 | Jacobs et al. ............... 623/1.34 |
| 6,492,615 B1 | 12/2002 | Flanagan | |
| 6,554,854 B1 | 4/2003 | Flanagan | |
| 6,679,980 B1 | 1/2004 | Andreacchi | |
| 6,692,522 B1 | 2/2004 | Richter | |

(Continued)

FOREIGN PATENT DOCUMENTS

| | | |
|---|---|---|
| WO | WO 98/29025 | 7/1998 |
| WO | WO 01/35864 | 5/2001 |
| WO | WO 2004/105647 | 12/2004 |

OTHER PUBLICATIONS

McGeough, J.A.; *Principals of Electrochemical Machining*; Chapman and Hall Ltd; pp. 1-10 and 118-121;1974.

(Continued)

*Primary Examiner* — David Isabella
*Assistant Examiner* — Suba Ganesan
(74) *Attorney, Agent, or Firm* — Vidas, Arrett & Steinkraus, P.A.

(57) ABSTRACT

A method for making an implantable stent includes the steps of (i) providing a plurality of elongate stent wires; (ii) forming said wires into a hollow tubular structure having opposed first and second open ends; (iii) terminating said wires at the second end; (iv) aligning the wires at the second end into a plurality of mated adjacent wires to define a plurality of abutting regions; (v) welding the mated adjacent wires to one and the other at the abutting regions to define a plurality of welds; and optionally (vi) chemically or electro-chemically removing a portion of the welds. The method may further include the steps of (a) extending at least one of the mated stent wires to provide an extended stent wire; (b) looping the extended stent wire so the extended end abuts a proximal pair of stent wires; and (c) welding the extended and looped wire to the proximal pair of wires. The step of looping may include the forming of the wire into an equilaterally arched loop having an apex, but not having other sharp bends.

38 Claims, 10 Drawing Sheets

U.S. PATENT DOCUMENTS

| | | |
|---|---|---|
| 7,655,039 B2 * | 2/2010 | Leanna et al. ............... 623/1.53 |
| 2002/0035396 A1 | 3/2002 | Heath |
| 2003/0024534 A1 | 2/2003 | Silvestri et al. |
| 2003/0065346 A1 * | 4/2003 | Evens et al. .................. 606/153 |
| 2004/0098099 A1 * | 5/2004 | McCullagh et al. ......... 623/1.15 |
| 2005/0049682 A1 | 3/2005 | Leanna et al. |

OTHER PUBLICATIONS

"Electropolishing of Nitinol", Admeds Schuessler; Advanced Micro Engineered Devices; Internet address: http://www.ademdes.com/processes/electropholishing-p.htm; Apr. 22, 2004.

* cited by examiner

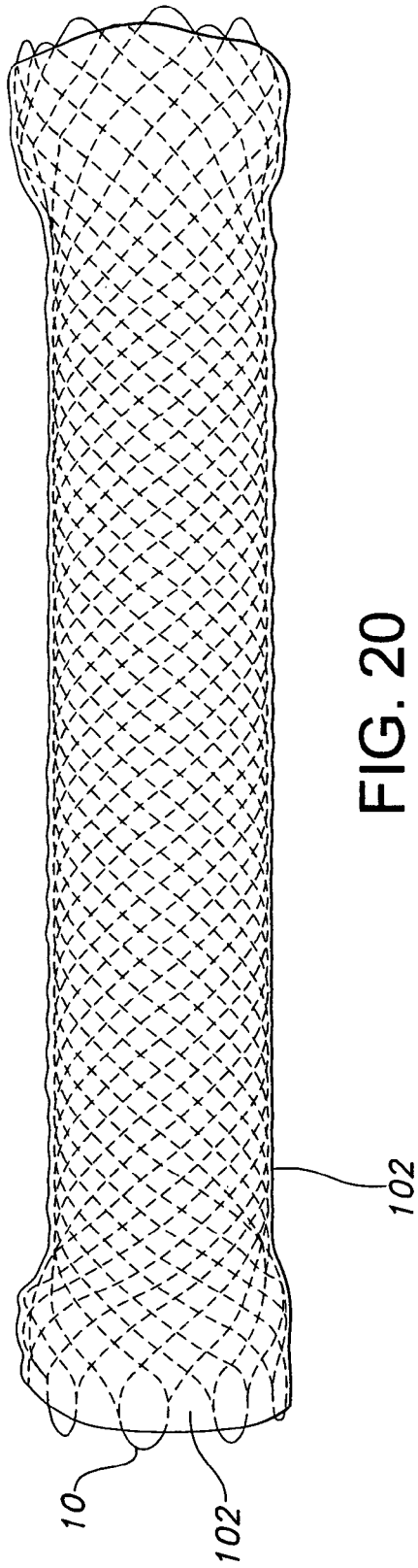
FIG. 20
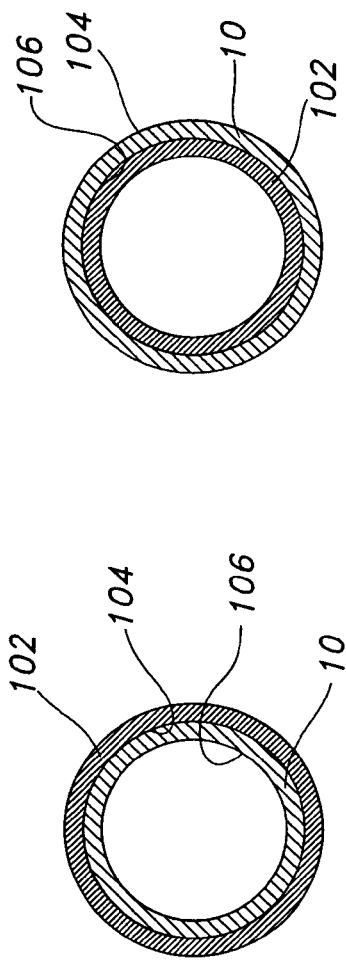
FIG. 21
FIG. 22

STENT WITH REDUCED WELD PROFILES AND A CLOSED-END WIRE CONFIGURATION

FIELD OF THE INVENTION

The present invention relates to stents having welded portions and atraumatic looped ends. The present invention also relates to such stents having their welded portions electro-chemically polished to reduce their profile and/or having a suture loop threaded at one or both extremities and/or being manufactured with a wire having a radiopaque core, and/or being fully or partially covered with a polymer such as silicone.

BACKGROUND OF THE INVENTION

Stents made from interconnecting, often braiding, elongate wires may be made less traumatic, i.e., atraumatic, by closing the loose wire ends at the ends of the stents. The loose wire ends have typically been closed by mechanical means, such as by clamps, for example clamped microtubes, or by welding. Such mechanical means, however, provide regions of high profile as compared to the other regions of the stents, see e.g., U.S. Pat. No. 6,083,257. The high profile regions are undesirable, often leading to deployment concerns, including higher deployment forces.

Electropolishing or electro-chemical polishing of laser cut nitinol stents to improve surface finishes has been previously mentioned, see e.g. U.S. Pat. No. 6,325,825 B1 and U.S. Patent Application Publication No. 2003/0024534 A1. Further, electro-polishing or electrochemical polishing services are available, see e.g. from Admedes Schuessler GmbH. Such polishing, however, has not been attempted to alleviate the above-discussed deployment concerns.

The present invention provides a stent made from elongate wires in a closed-end design while avoiding the disadvantages of the prior art. More particularly, the present invention is directed to certain advantageous closed-end stent loop designs having reduced profiles to lower deployment forces and ease deployment of the stent.

SUMMARY OF THE INVENTION

In one aspect of the present invention is a method for making an implantable stent. The method comprises the steps of (i) providing a plurality of elongate stent wires; (ii) forming the wires into a hollow tubular structure having opposed first and second open ends; (iii) terminating the wires at the second end; (iv) aligning the wires at the second end into a plurality of mated adjacent wires to define a plurality of abutting regions; (v) welding the mated adjacent wires to one and the other at the abutting regions to define a plurality of welds; and, optionally, (vi) chemically or electro-chemically removing a portion of the welding material from the plurality of welds. Desirably, the mated adjacent wires are substantially parallel to one and the other at the abutting regions.

In this aspect of the present invention, the step of welding may include the step of providing an inert gas proximal to the weld areas. Further, the step of welding includes laser welding, electron beam welding, resistance welding, tungsten inert gas welding, metal inert gas welding, and combinations thereof.

Desirably, the step of forming the tubular structure comprises braiding the wires, winding the wires, knitting the wires, and combinations thereof, preferably braiding the wires. The material of the wires and the material of the welds may be the same type of material.

Further, the stent wire may include a radiopaque material.

The step of chemically or electro-chemically removing the portion of the welding material may include chemical polishing or etching, chemical deburring, electrochemical polishing or etching, jet-electropolishing and combinations thereof. The step of electro-chemically removing the portion of the welding material further includes the step of providing an electrolyte, where the electrolyte is selected from the group consisting of $NaClO_3$ electrolyte, $NaNO_3$ electrolyte, NaCl electrolyte, $Na_2Cr_2O_7$ electrolyte, $HOCH_2CH_2OH$ electrolyte, and combinations thereof.

In further detail, the step of electro-chemically removing the portion of the welding material may further include the step of (i) providing an electrolyte; (ii) placing a cathode into the electrolyte; (iii) placing a portion of the stent having the welding material into the electrolyte; (iv) providing an electrical voltage or current so that the cathode is negatively charged and the stent portion is positively charged; and (v) partially dissolving the portion of the stent exposed to the electrolyte.

In another aspect of the present invention, the method of making the stent may further include the steps of (i) extending at least one of the mated stent wires to provide an extended stent wire; (ii) looping the extended stent wire so the extended end abuts a proximal pair of stent wires; and (iii) welding extended and looped wire to the proximal pair of wires. Desirably, the step of looping includes forming the wire into an arch with equilateral sides, having an apex, but not having other sharp bends. Desirably, the step of looping includes forming the wire into an equilateral arch having one vertex having similar curvatures on either side of the one vertex, where the equilateral arch does not contain a second vertex having dissimilar curvatures on either side of the second vertex.

In another aspect of the present invention, the method of making the stent may further include the steps of (i) extending at least one of the mated stent wires past the abutting regions to provide an extended stent wire; and (ii) looping the extended stent wire at its extended end to form a coil thereat. A plurality of extended wires may also be formed into one coil or pig tail.

Desirably, the elongate wires comprise biocompatible materials selected from the group consisting of nitinol, stainless steel, cobalt-based alloy such as Elgiloy, platinum, gold, titanium, tantalum, niobium, and combinations thereof, preferably nitinol. The elongate wires may be composite wires for improved radiopacity, such as having an inner core of tantalum, gold, platinum, iridium or combination of thereof and an outer layer or member of nitinol.

In another aspect of the present invention, an implantable stent is provided. The stent of this aspect of the present invention may include a plurality of wires arranged to form a hollow tubular structure having a tubular wall to define an interior surface and an exterior surface and having opposed open first and second ends, where the wires terminate at the second open end ends and adjacently abutting wires are welded at the second open end with a welding material to provide welds, and further where at least a portion of the welded material has been removed to reduce the profile of the welds. Desirably, the portion of welded material has been removed by chemical or electro-chemical polishing. Preferably, at least 25 to 50% by weight of the stent material at or around the weld location has been removed. The reduced profile of the welds are from about 5 to about 50 linear percent of a diameter of the stent wires.

The stent includes wires made from biocompatible materials, such as nitinol, stainless steel, cobalt-based alloy such as Elgiloy, platinum, gold, titanium, tantalum, niobium, and combinations thereof. The weld material and the wire material may also be the same, for example nitinol. Further, the elongate wires have an inner core of tantalum gold, platinum, iridium or combination of thereof and an outer member of nitinol.

In another aspect of the present invention, at least one some of the adjacently abutting stent wires are extended past the welds and looped into an arch with equilateral sides having an apex, but not having other sharp bends, or in other words at least some of the adjacently abutting stent wires are extended past the welds and looped into an arch with equilateral sides having one vertex having similar curvatures on either side of the one vertex, where the arch design does not contain a second vertex having dissimilar curvatures on either side of the second vertex. Alternatively, at least some of the adjacently abutting stent wires are extended past the welds and looped to form a coil thereat in the shape of a pig tail. Still alternatively, at least some of the adjacently abutting stent wires are extended past the welds and looped to form one coil thereat.

The stent wires may be coated, for example coated with silicone. Further, the stent may be fully or partially covered with a polymeric covering, such as silicone, in order to prevent tissue or tumor ingrowth.

The stent may further include a hollow tubular graft disposed over the interior or the exterior surface. The graft may be a polymeric material, for example, a polyester, a polypropylene, a polyethylene, a polyurethane, a polynaphthalene, a polytetrafluoroethylene, an expanded polytetrafluoroethylene, a silicone, and combinations thereof.

Desirably, the stent is a braided stent.

The stent may further include a polymeric ring disposed over the exterior surface at the second open end. Additionally, the stent may further include a suture secured to one of the open ends. Such suture or sutures are useful for positioning, repositioning, and/or removing the stent. The suture can be a metallic, polymeric or textile suture loop threaded through the stent loops at one or both extremities of the stent. The suture loop may include a protruding part to help facilitate the capture or grabbing of the stent end.

In another aspect of the present invention, an implantable stent includes a plurality of wires arranged to form a hollow tubular structure having a tubular wall to define an interior surface and an exterior surface and having opposed open first and second ends, where the wires terminate at the second open end ends and adjacently abutting wires are welded at the second open end with a welding material to provide welds, and further where at least a portion of the welded material has been removed by chemical or electrochemical polishing to reduce the profile of the welds.

BRIEF DESCRIPTION OF THE DRAWINGS

FIG. 20 depicts a stent having a covering of silicone according to the present invention.

FIG. 21 is a cross-sectional view if the stent of FIG. 20 showing an outer covering of silicone about the stent.

FIG. 22 is a cross-sectional view if the stent of FIG. 20 showing an inner covering of silicone about the stent.

DETAILED DESCRIPTION OF THE PREFERRED EMBODIMENT

Figure 1:
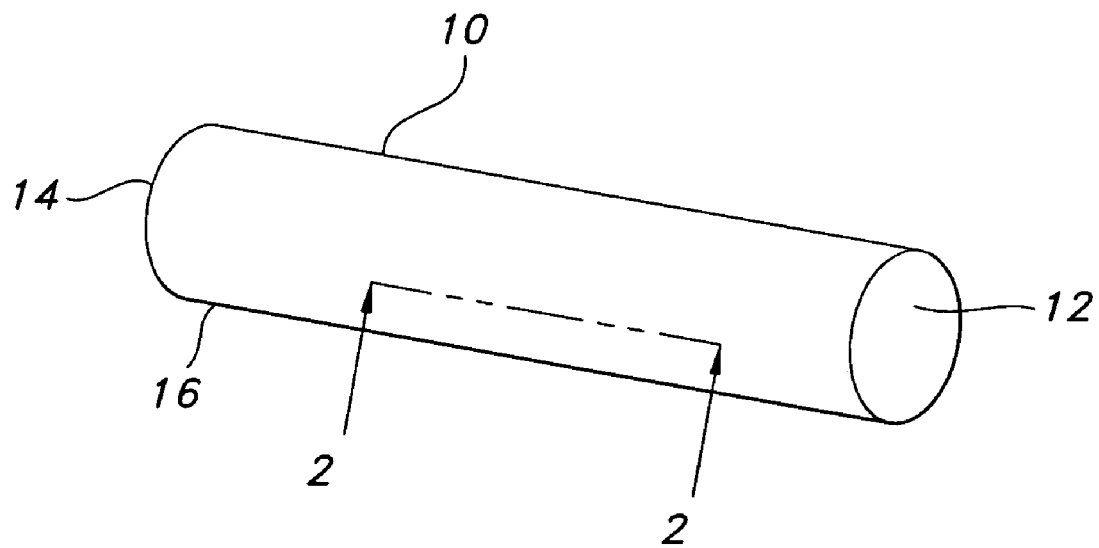
FIG. 1 is a perspective view of a hollow, tubular stent according to the present invention.
Figure 2:
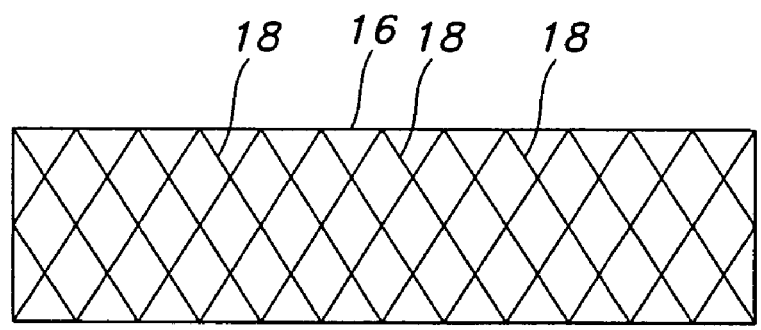
FIG. 2 is an expanded view of a wall portion of the stent of FIG. 1 taken along the 2-2 axis showing a plurality of stent wires.

The present invention overcomes the deficiencies of the prior art by providing, among other things, low profile stent welds that reduce stent deployment forces. FIG. 1 depicts stent 10 of the present invention. Stent 10 is a hollow tubular structure having opposed open ends 12, 14 and having a tubular wall 16 therebetween. A portion of the tubular wall 16 is depicted in FIG. 2 as having a plurality of elongate wires 18 formed into the tubular wall 16. The elongate wires 18 traverse the length of the stent 10 in a direction traverse to the longitudinal length of the stent 10. The elongate wires 18 may be formed into the tubular wall 16 by braiding the wires 18, winding the wires 18, knitting the wires 18, and combinations. Preferably, the wires 18 are braided to form the tubular wall 16.

Figure 3:
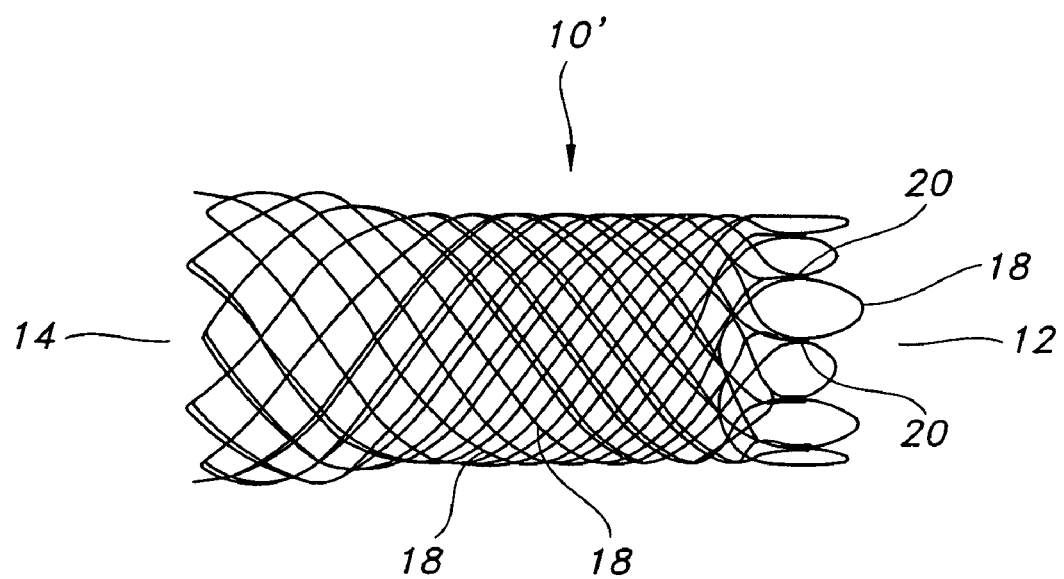
FIG. 3 depicts a braided stent with a closed-end loop design having a plurality of welds at the closed end according to the present invention.
Figure 4:
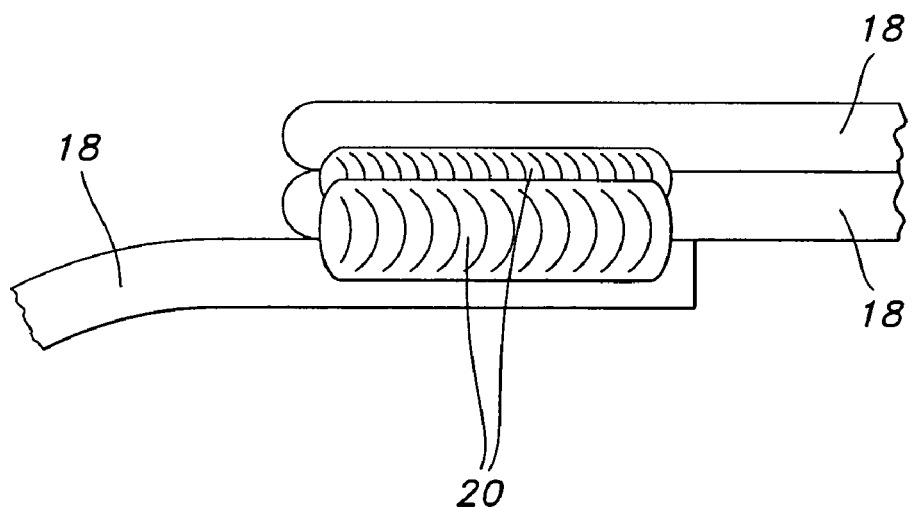
FIG. 4 is an expanded view of a weld of FIG. 3.

A welded stent 10' according to the present invention is depicted in FIG. 3. The elongate wires 18 terminating at open end 12 are mated and adjacently mated wires are secured to one and the other by welds 20. The joining of three adjacently mated wires 18 and the welding thereat is depicted in further detailed in FIG. 4. The positioning of adjacently mated wires to form closed-loop end designs, excluding the closed-end arch loop design of the present invention which is described below, is further described in U.S. Application No. 60/472,929, filed May 23, 2003, which represents U.S. application Ser. No. 10/852,495 and which published as US 2005/0049682 A1, the contents of which are incorporated herein by reference. The weld 20 may be a low profile weld, i.e., a weld with a reduced welding zone as compared to stent welds of the prior art. The stent 10' depicted in FIG. 3 includes 24 wires 18 of nitinol or nitinol-containing material. The wires are relatively thin at a diameter of about 0.011 inches. The number of wires and the diameters of the wires, which may be the same or different, depicted in FIG. 3 are not limiting, and other numbers of wires and other wire diameters may suitably be used.

A pair of adjacently welded wires according to the present invention is depicted in FIGS. 5-8. Weld 24 securably joins adjacently mated stent wires 22. As compared to the prior art, the weld 24 of the present invention has a significant reduction in the amount of welding material in weld 24. Desirably, weld 24 has at least about 25% or less welding material than prior art welds, for example from about 25% to about 50% less welding material. Alternatively, the weld 24 desirably has a profile, i.e., a depth $d_3$ and/or a width $d_4$, that is less than the diameter, $d_1$, of the wire 22. Yet alternatively, or in addition to, the welds 24 of the present invention have a profile of about 150 microns or less, preferably from about 50 microns to about 150 microns. Yet alternatively, or in addition to, the weld 24' of the present invention and portions of the stent wires 22' proximal to the welds 24' have a reduced profile where the profile of weld 24' is lower than the profile of weld 24 and where the diameter, $d_2$, of the proximal stent portions 22' is less than the diameter, $d_1$, of stent wire portions 22. The mass and volume of the weld 24' and/or stent portions 22' is suitably reduced by chemical or electrochemical polishing. Reduced profile welds 24, 24' of the present invention overcome the difficulty of constraining the stent 10, 10' on a delivery device (not shown) by removing excess weld material that would otherwise increase localized constraining forces at the weld locations as compared to other portions of the stent 10, 10'.

Useful welding methods include, but are not limited to, laser welding, electron beam welding, resistance welding, tungsten inert gas welding, metal inert gas welding and combinations thereof. In laser and electron beam welding the wires are partially melted by the energy provided by the laser or electron beam. In gas tungsten arc welding (GTAW or TIG welding), an arc is formed between an electrode, typically tungsten, and the metal being welded. In metal inert gas (MIG) welding, an arc is generated between a filler electrode and the metal being welded with metal melted from the filler electrode being added to the metal being welded. Resistance welding uses the application of electric current and sometimes mechanical pressure to create a weld between two pieces of metal. The weld areas may be shielded with an inert gas. Suitable, but non-limiting, inert gasses include argon and argon/gas admixtures, such as argon/hydrogen or argon/helium.

Figure 9:
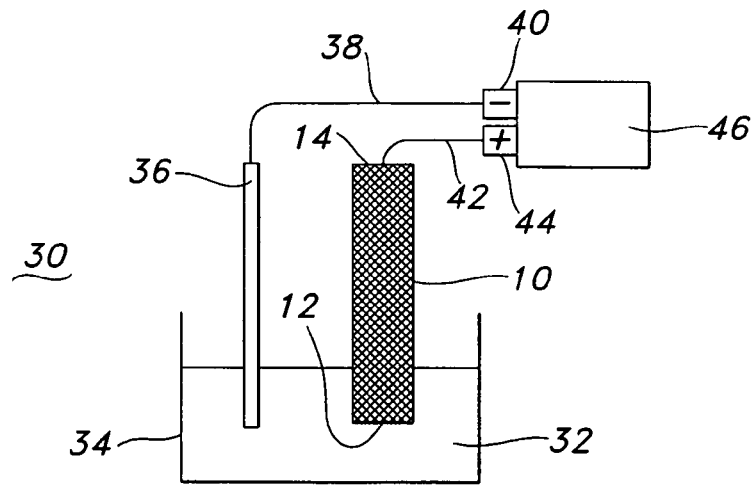
FIG. 9 is a schematic depiction of an electro-chemical polishing cell according to the present invention.
Figure 10:
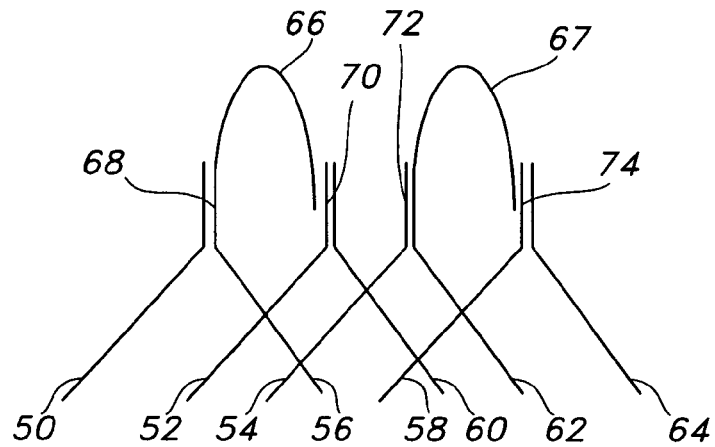
FIGS. 10-14 depict an arch with equilateral sides and an apex in a closed-end loop design according to the present invention.

FIG. 9 depicts an electro-chemical cell 30 for removing weld material to thereby form the low profile weld 24, 24' of the present invention. The cell 30 includes an electrolyte 32 contained within a container 34. The stent 10 with welds 24, 24' at stent end 12 is placed within the electrolyte 32. A cathode 36 is also placed within the electrolyte 32. A wire 38 connects the cathode 36 to the negative terminal 40 of voltage or current source 46. A wire 42 connects the stent 10 to the positive terminal 44 of the voltage or current source 46. Upon application of voltage or current from the source 46 the cell 30 becomes operational. Material, such as weld material, is dissolved from the stent 10 into the electrolyte 32. Useful electrolytes include $NaClO_3$ electrolyte, $NaNO_3$ electrolyte, $NaCl$ electrolyte, $Na_2Cr_2O_7$ electrolyte, $HOCH_2CH_2OH$ electrolyte and combinations thereof. Typical, but non-limiting, current densities are in the magnitude of about 50 to about 150 amps/cm$^2$. The electrolyte 32 may be in motion at low velocities or unstirred. As the anode metal is dissolved electrochemically, the dissolution rate is not influenced by the hardness or other physical characteristics of the metal.

Desirably, the wires 22 are made from nitinol, stainless steel, cobalt-based alloy such as Elgiloy, platinum, gold, titanium, tantalum, niobium, and combinations thereof. Further, the wires 22 have an inner core of tantalum gold, platinum, iridium or combination of thereof and an outer member or layer of nitinol to provide a composite wire for improved radiocapicity or visibility. Further details of such composite wires may be found in U.S. Patent Application Publication 2002/0035396 A1, the contents of which is incorporated herein by reference. Preferably, the wires 22 are made from nitinol. Further, the filling weld material, if required by welding processes such as MIG, may also be made from nitinol, stainless steel, cobalt-based alloy such as Elgiloy, platinum, gold, titanium, tantalum, niobium, and combinations thereof, preferably nitinol. The material of the cathode is no critical and can be made out of any suitable metal. The filling weld material and the wire 22 may be made of the same material, for example nitinol.

As the chemical electro-chemical polishing 30 removes material from portions of the stent 10 that are disposed within the electrolyte 32, there are several means to selectively remove material from the stent 10, such as welds 24, 24', burrs or other imperfections (not shown), and the like. One technique for selectively removing material is through the use of a photoresist or insulator, which is an organic polymer or resin that can be applied to selective areas of the stent 10 to avoid the electro-chemical polishing of covered parts 30 as the photoresist insulates the selected from the action of the electrolyte. For example, as depicted in FIG. 5A, portions of the stent wires 22 may be coated with a photoresist 48 prior to placement in the cell 30. After chemical or electro-chemical polishing is completed the photoresist 48 may be removed by application of a suitable solvent. Alternatively, jet electro-chemical polishing or etching could be used to specifically etch weld regions. Jet etching includes the localized application of electrolyte at moderate velocity, such as about 3 to about 30 m/s, to selectively polish desired areas, such as stent welds.

Alternatively, chemical polishing, chemical etching and the like may be used to remove portions of the weld 24, 24' and optionally portions of the stent wire 22. Chemical polishing or etching is similar to the above described electro-chemical methods, expect an oxidizing acid is added to the electrolyte and associated equipment (current or voltage source, cathode, etc.) is optionally not necessary. Useful, but not limiting, oxidizing acid-containing electrolytes include electrolytes having hydrofluoric acid, nitric acid, and combinations thereof.

Figure 5:
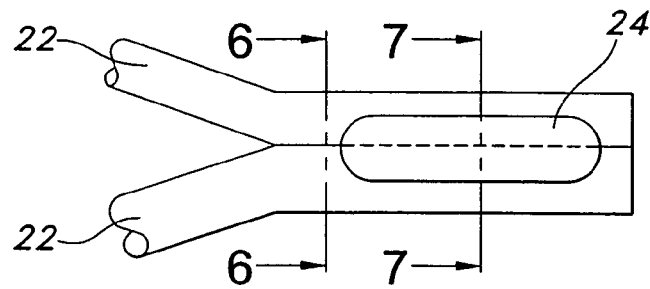
FIG. 5 depicts a weld adjoining two stent wires according to the present invention.
Figure 5A:
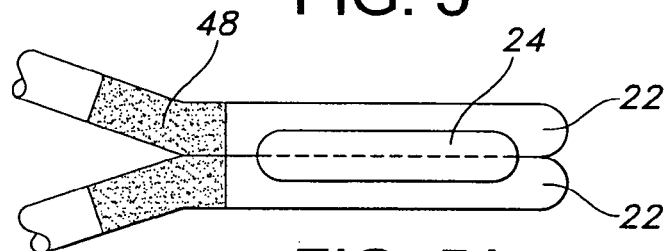
FIG. 5A depicts a weld adjoining two stent wires having an insulator or photoresist on selected stent wire portions according to the present invention.
Figure 6:
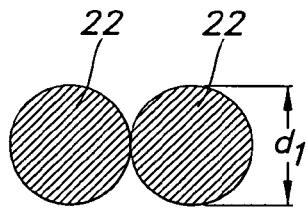
FIG. 6 is a cross-sectional view of the adjoining stent wires of FIG. 5 taken along the 6-6 axis.
Figure 7:
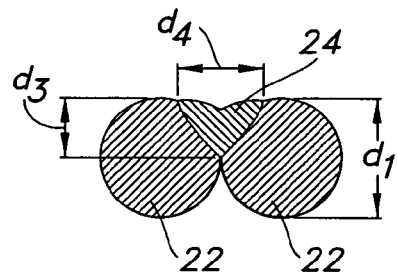
FIG. 7 is a cross-sectional view of the welded stent wires of FIG. 5 taken along the 7-7 axis.
Figure 8:
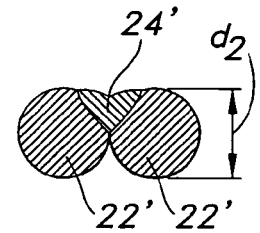
FIG. 8 is a cross-sectional view of the welded stent wires of FIG. 7 after chemical or electrochemical polishing.

The present invention, however, is not limited to low profile welds just at terminatingly adjacent wires, such as wires 22 of FIG. 5 or 5A. As depicted in FIGS. 10-14, certain stent wires 56, 62 may be extended beyond adjacent wires 50, 64, and then looped back to proximal wires 52, 60 and 58, 64, respectively. Adjacent portions of wires 50 and 56 are abuttingly disposed at abutting region 68. Similarly, adjacent portions of wires 52 and 60 and the adjacent portion of the extended loop portion 66 are abuttingly disposed at abutting region 70; adjacent portions of wires 54 and 62 are abuttingly disposed at abutting region 72; and adjacent portions of wires 58 and 64 and the adjacent portion of the extended loop portion 67 are abuttingly disposed at abutting region 74. Desirably, the abuttingly disposed wire portions in the abutting regions are substantially parallel to one and the other, for example, but not limited to, being within about plus or minus 10 degrees of parallelism to one and the other, preferably, but not limited to within about plus or minus 5 degrees of parallelism.

Figure 11:
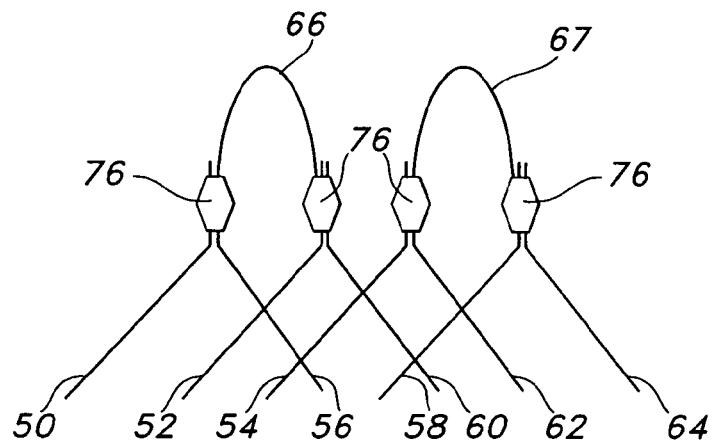

As depicted in FIG. 11, the wires at the abutting regions 68, 70, 72, 74 may be secured by welds 76. Desirably, welds 76 are low profile welds having low profiles from electrochemical polishing according to the present invention.

Figures 12, 13, 14:
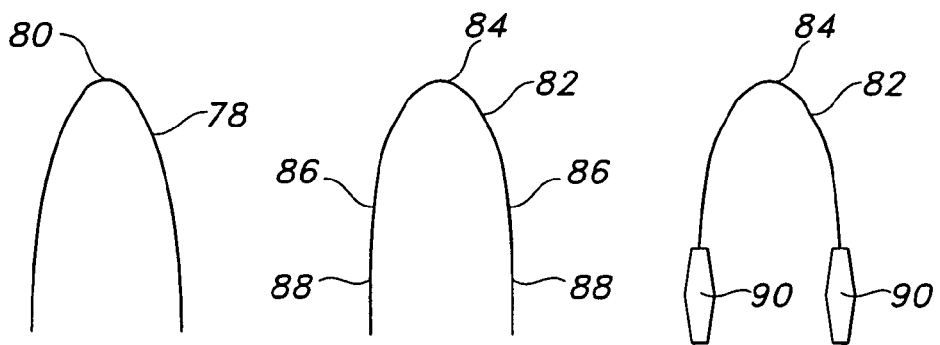

Desirably, the extended loop portions 66, 67 are of an arch with equilateral sides design, which can be referred to as a cathedral type of arch or loop. As depicted in FIG. 12, the equilaterally arched loop 78 has an apex or vertex 80. As used herein, the term "vertex" and its variants refer to the intersection of two geometric lines or curves. As used herein, the term "apex" and its variants refer to a vertex at the top or summit of a loop. Desirably, the equilaterally arched loop 78 does not have any bends, which are defined as areas having dissimilar curvatures on either side of a point, except for the apex 80. In other words, the equilaterally arched loop 78 has an apex, but not other sharp bends. Desirably, the equilaterally arched loop 78 has one vertex (or apex 80) having similar curvatures on either side of the one vertex (or apex 80), but does not contain a second vertex having dissimilar curvatures on either side of the second vertex.

The equilaterally arched loop design offers several advantages, including reduced deployment force, as compared to prior art loop designs having a plurality of vertices or sharp bends. When a stent is constrained on or in a delivery system (not shown) the multiple sharp bends in the end loops of the stent typically impinge on the wall of the delivery system and become slightly imbedded thereat, thereby distorting the outer sheath of the delivery system. This results in significantly greater deployment force values. Further, as the equilaterally arched loop has only one sharp bend, i.e., its apex, and is defined otherwise by a gradual curvature, the gradual curvature portions do not become imbedded in the wall of the delivery system, thereby significantly reducing the resultant deployment force.

Figure 19:
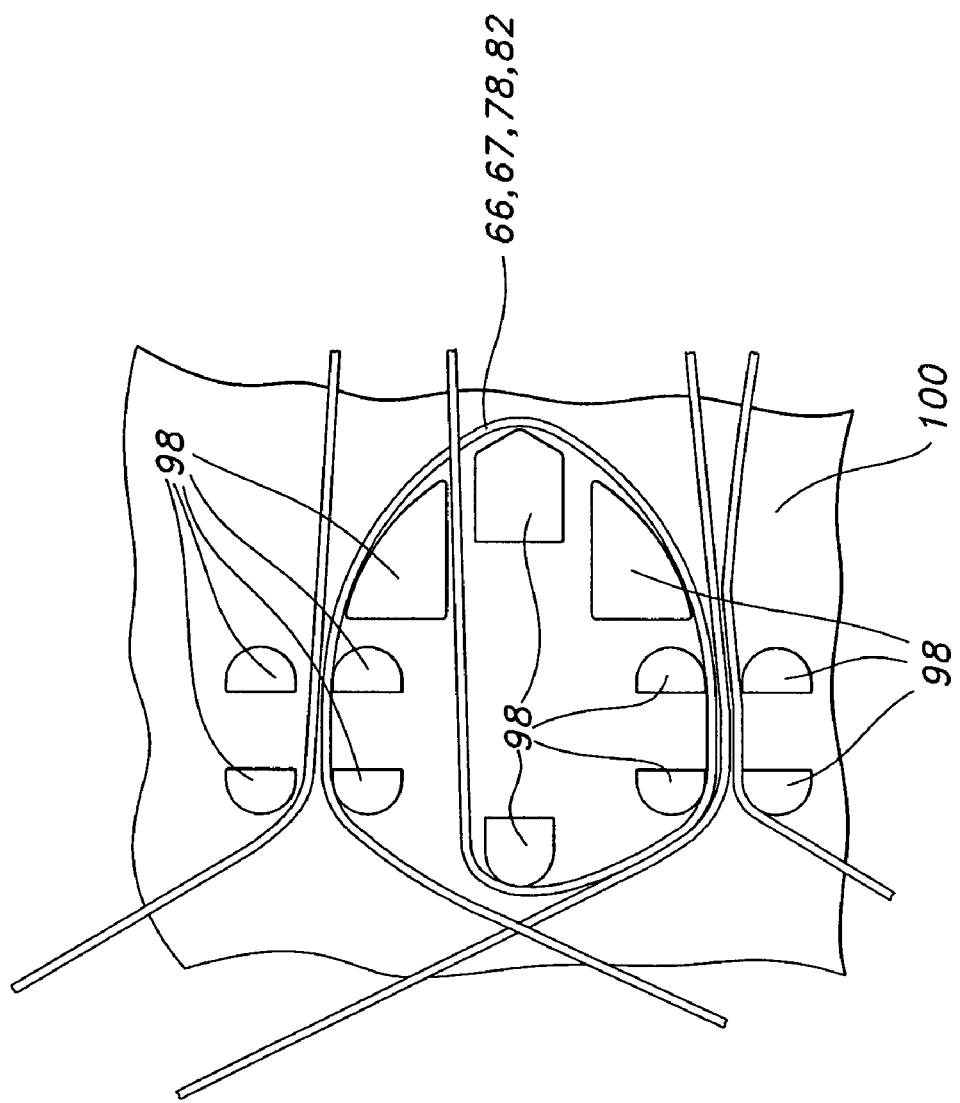
FIG. 19 depicts a mandrel having shaped pins for forming the closed loops of FIGS. 10-14.

In another aspect of the present invention as depicted in FIG. 13, an equilaterally arched loop 82 may have an apex 84 and vertices 86 having substantially straight line portions 88. In such a case, the vertices 86 and the straight line portions 88 have low profile welds 90 thereover to adjoin other adjacently abutting stent wires (not shown). The equilaterally arched loops 66, 67, 78, 82 of the present invention may be suitably formed by winding their stent wires about shaped pins 98 on a mandrel 100 as depicted in FIG. 19. Further, either or both of the ends 12, 14 of the stent 10, 10', including end 12 with equilaterally arched loops 66, 67, 78, 82, may have a suture or sutures (not shown) attached thereto. Such sutures are useful for positioning, repositioning, and/or removing the stent 10, 10'.

Figure 15:
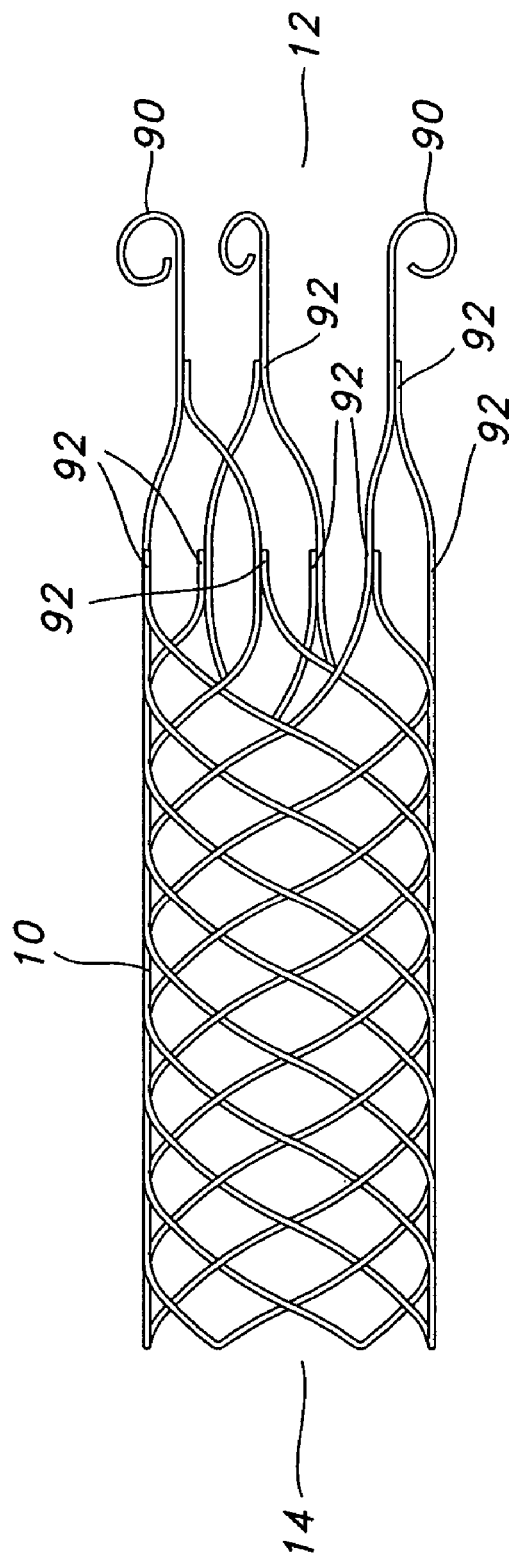
FIG. 15 depicts another embodiment according to the present invention of a closed-end loop design of the present invention having a plurality of coils at the closed end.
Figure 16:
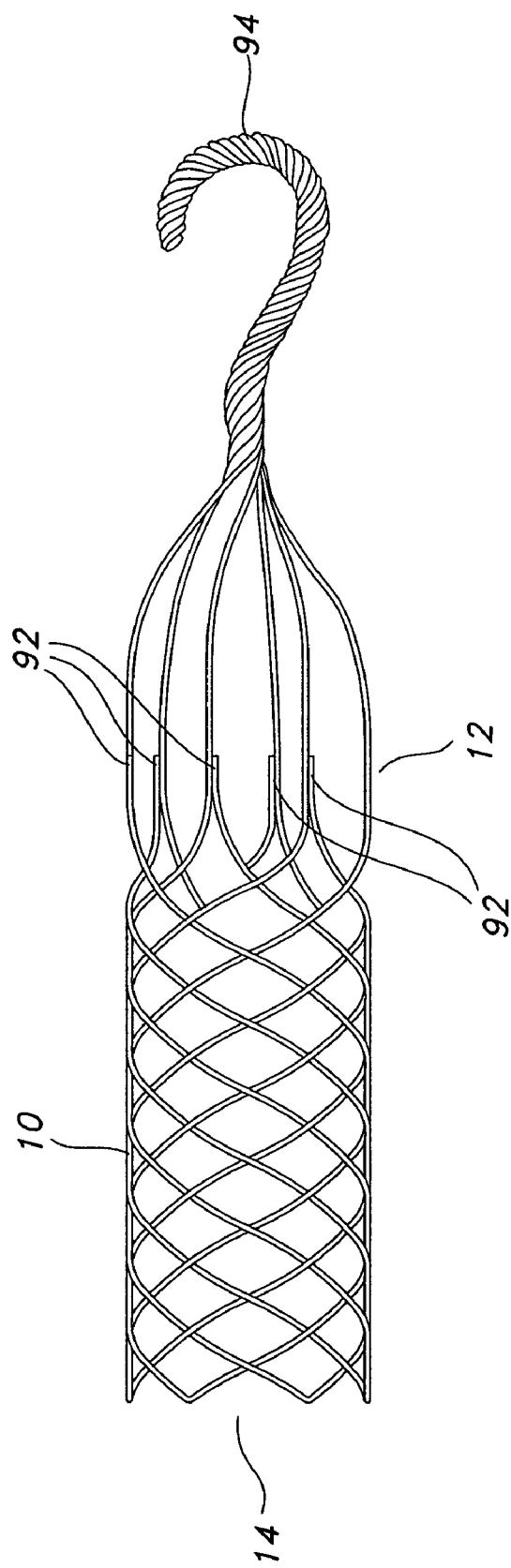
FIG. 16 depicts yet another embodiment according to the present invention of a closed-end loop design of the present invention having one coil or pigtail at the closed end.
Figure 17:
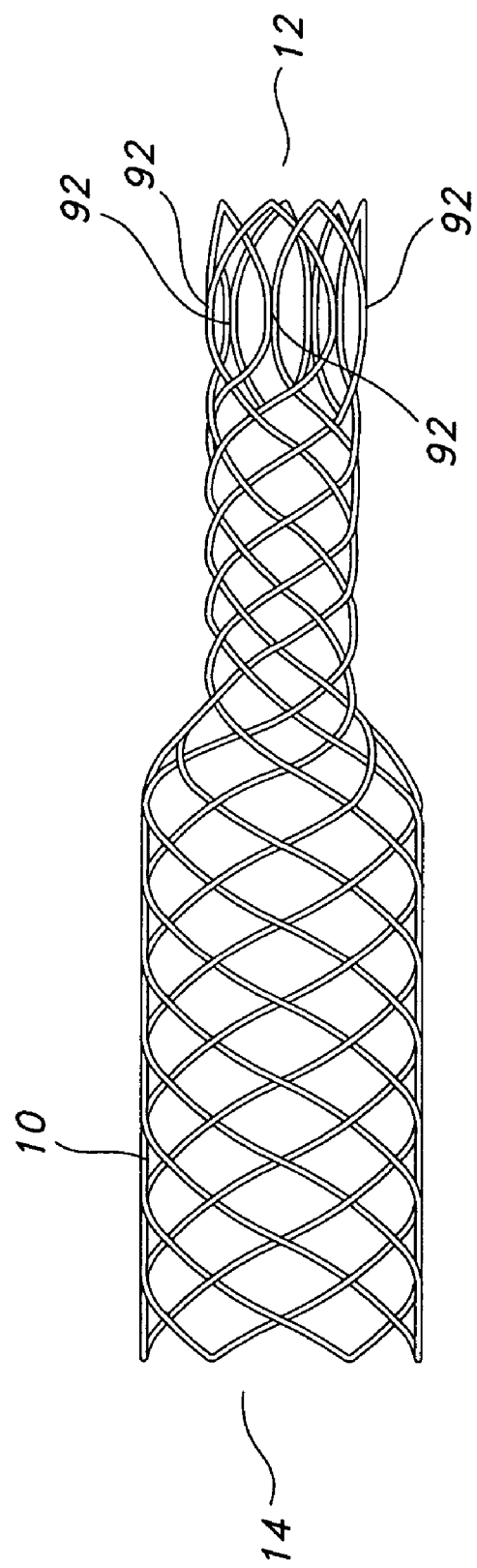
FIGS. 17-18 depict yet another embodiment according to the present invention of a closed-end design having a band disposed over the stent wires at the closed end.
Figure 18:
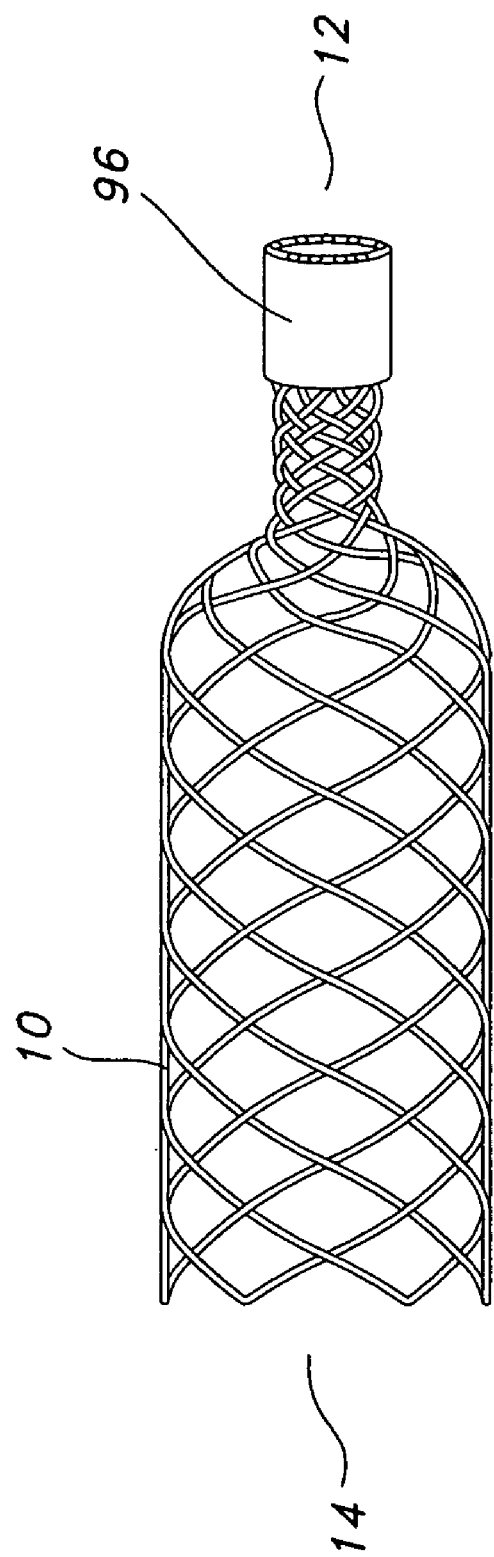

In still a further aspect of the present invention, the stent 10 may have other designs at open end 12 that are useful for positioning, repositioning, and/or removing stent 10. As depicted in FIG. 15, wires may be extended from all or some of the adjacent wire engaging portions 92. The ends of the extended wires may be formed into coils 90. As depicted in FIG. 16, wires may be extended from all or some of the adjacent wire engaging portions 92. The ends of the extended wires may be formed into a coil 94, which is in the shape of a hook and commonly referred to as a pigtail. Still further, the open end 12 of stent 10 may be of reduced diameter as compared to the other portions of the stent 10. The reduced diameter portion facilitates access to the stent end 12 for positioning, repositioning, and/or removing stent 10. The stent end 12 of the stent 10 of FIG. 17 may include any of the previously described loops or coils thereat. Alternatively, or in addition to, the stent end 12, as depicted in FIG. 18, may have a band 96 disposed thereover, which is also useful for positioning, repositioning, and/or removing stent 10. Band 96 may be made of any biocompatible material, including polymers, plastics and metals. The band 96 may be attached to the stent end 12 by adhesive, mechanical or physical means, such as adhesive bonding, welding, suturing, fusing, and the like.

As depicted in FIG. 20, the stent 10 may be fully, substantially or partially covered with silicone 102 in also the form of a tubular structure. The silicone 102 may be disposed on external surfaces 104 of the stent 10, as depicted in FIG. 21, or disposed on the internal surfaces 106 of the stent 10, as depicted in FIG. 22, or combinations thereof.

With any embodiment of the stent 10, 10' is usable to maintain patency of a bodily vessel, such as in the coronary or peripheral vasculature, esophagus, trachea, bronchi colon, biliary tract, urinary tract, prostate, brain, and the like. Also, the stent 10, 10' may be treated with any of the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. An implantable stent comprising:
 a plurality of wires arranged to form a hollow tubular structure having a tubular wall to define an interior surface and an exterior surface and having opposed open first and second ends,
 wherein the wires terminate at said second open end and an adjacently abutting pair of wires are welded at said second open end with a welding material to provide a first weld consisting of two wires and the welding material welded together,
 wherein at least one of the adjacently abutting stent wires is extended past the first weld to define an extended wire and looped into an equilaterally arched loop having an apex having similar curvatures on either side of said apex, but not having other bends so that the extended wire adjacently abuts a proximal pair of parallel wires to define three substantially parallel wires, wherein the three substantially parallel wires are welded directly to each other with the welding material to provide a second weld, and further wherein at least about 25% to about 50% by weight of the welded material has been removed by selective chemical or electro-chemical polishing to reduce the profile of the first and second welds to less than a diameter of the wires.

2. The stent of claim 1, wherein said welding material is formed from said adjacently abutting wires.

3. The stent of claim 1, wherein said welding material is a filling material.

4. The stent of claim 1, wherein a portion of the adjacently abutting wires proximal to said welds has been removed by chemical or electro-chemical polishing.

5. The stent of claim 4, where at least about 25% to about 50% by weight of the stent material at the weld location has been removed.

6. The stent of claim 1, wherein the reduced profile of the welds are from about 5 to about 50 linear percent of the diameter of the stent wires.

7. The stent of claim 1, wherein the wires comprise a biocompatible material selected from the group consisting of nitinol, stainless steel, cobalt-based alloy, platinum, gold, titanium, tantalum, niobium, and combinations thereof.

8. The stent of claim 7, wherein the weld material and the wire material are the same.

9. The stent of claim 7, wherein the weld material and the wire material are nitinol.

10. The stent of claim 7, wherein the elongate wires have an inner core of tantalum gold, platinum, iridium or combination of thereof and an outer portion of nitinol.

11. The stent of claim 1, wherein the stent is coated with silicone.

12. The stent of claim 1, wherein the stent is partially or fully covered with silicone.

13. The stent of claim 1, further comprising a hollow tubular graft disposed over the interior or the exterior surface.

14. The stent of claim 13, wherein the graft is a polymeric material.

15. The stent of claim 14, wherein the polymeric material is selected from the group consisting of polyester, polypropylene, polyethylene, polyurethane, polynaphthalene, polytetrafluoroethylene, expanded polytetrafluoroethylene, silicone, and combinations thereof.

16. The stent of claim 1, wherein the stent is a braided stent.

17. The stent of claim 1, further including a metal or suture loop secured to one of said open ends.

18. The stent of claim 1, wherein the profile of the welds is defined by a depth and/or a width of the welds.

19. The stent of claim 18, wherein the depth of the welds is about 150 microns or less and wherein the width of the welds is about 150 microns or less.

20. The stent of claim 18, wherein the profile of the welds is from about 50 microns to about 150 microns.

21. The stent of claim 18, wherein the depth of the welds is from about 50 microns to about 150 microns.

22. The stent of claim 18, wherein the width of the welds is from about 50 microns to about 150 microns.

23. The stent of claim 18, wherein the depth of the welds is from about 50 microns to about 150 microns and wherein the width of the welds is from about 50 microns to about 150 microns.

24. An implantable stent comprising:

a plurality of wires arranged to form a hollow tubular structure having a tubular wall to define an interior surface and an exterior surface and having opposed open first and second ends, wherein the wires terminate at said second open end and an adjacently abutting pair of wires are welded at said second open end with a welding material to provide a first weld consisting of two wires and the welding material welded together, wherein at least one of the adjacently abutting stent wire is extended past the first weld to define an extended wire and looped into an equilaterally arched loop having an apex, but not having other bends so that an end of the extended wire adjacently abuts a proximal pair of wires, wherein the end of the extended wire and the proximal pair of wires are welded directly to each other with the welding material to provide a second weld;

wherein said apex has similar curvatures on either side of said apex and said equilaterally arched loop does not contain a second vertex having dissimilar curvatures; and wherein at least about 25% to about 50% by weight of the welding material has been removed by selective chemical or electro-chemical polishing to reduce the profile of the first and second welds to less than a diameter of the wires.

25. The stent of claim 24, wherein the wires comprise a biocompatible material selected from the group consisting of nitinol, stainless steel, cobalt-based alloy, platinum, gold, titanium, tantalum, niobium, and combinations thereof.

26. The stent of claim 24, wherein the elongate wires have an inner core of tantalum gold, platinum, iridium or combination of thereof and an outer portion of nitinol.

27. The stent of claim 24, wherein the stent is coated with silicone.

28. The stent of claim 24, wherein the stent is partially or fully covered with silicone.

29. The stent of claim 24, further comprising a hollow tubular graft disposed over the interior or the exterior surface.

30. The stent of claim 29, wherein the graft is a polymeric material.

31. The stent of claim 30, wherein the polymeric material is selected from the group consisting of polyester, polypropylene, polyethylene, polyurethane, polynaphthalene, polytetrafluoroethylene, expanded polytetrafluoroethylene, silicone, and combinations thereof.

32. The stent of claim 24, wherein the stent is a braided stent.

33. The stent of claim 24, wherein the profile of the welds is defined by a depth and/or a width of the welds.

34. The stent of claim 33, wherein the profile of the welds is about 150 microns or less.

35. The stent of claim 33, wherein the depth of the welds is about 150 microns or less.

36. The stent of claim 33, wherein the width of the welds is about 150 microns or less.

37. An implantable stent comprising:

a plurality of wires arranged to form a hollow tubular structure having a tubular wall to define an interior surface and an exterior surface and having opposed open first and second ends, wherein the wires terminate at said second open end with adjacently abutting two substantially parallel wires and adjacently abutting three wires substantially parallel in an alternating sequence, wherein the adjacently abutting and substantially parallel two wires are welded directly with a welding material to form a first weld consisting of the two wires and the welding material welded together, and the other and the adjacently abutting and substantially parallel three wires are welded directly to one and the other at said second open end with a welding material to provide a second weld, and further wherein at least about 25% to about 50% by weight of the welding material has been removed by selective chemical or electro-chemical polishing to reduce a depth and/or a width of the welds to about 150 microns or less.

38. An implantable stent comprising:

a plurality of wires arranged to form a hollow tubular structure having a tubular wall to define an interior surface and an exterior surface and having opposed open first and second ends, wherein the wires terminate at said second open end and an adjacently abutting pair of wires are welded at said second open end with a welding material to provide a first weld consisting of two wires and the welding material welded together, wherein at least one of the adjacently abutting stent wires is extended past the first weld to define an extended wire and looped into an equilaterally arched loop having an apex so that the extended wire adjacently abuts a proximal pair of wires where the extended wire and the proximate pair of wires are substantially parallel to each other, wherein the three substantially parallel wires are welded directly to each other with the welding material to provide a second weld, wherein said apex has similar curvatures on either side of said apex and said equilaterally arched loop does not contain a second vertex having dissimilar curvatures on either side of the second vertex, and wherein at least about 25% to about 50% by weight of the welded material has been removed by selective chemical or electro-chemical polishing to reduce the profile of the first and second welds to less than a diameter of the wires.

* * * * *